(12) United States Patent
Yoshida

(10) Patent No.: US 11,839,022 B2
(45) Date of Patent: Dec. 5, 2023

(54) CIRCUIT BOARD

(71) Applicant: SHINKO ELECTRIC INDUSTRIES CO., LTD., Nagano (JP)

(72) Inventor: Kazuhiro Yoshida, Nagano (JP)

(73) Assignee: SHINKO ELECTRIC INDUSTRIES CO., LTD., Nagano (JP)

( * ) Notice: Subject to any disclaimer, the term of this patent is extended or adjusted under 35 U.S.C. 154(b) by 11 days.

(21) Appl. No.: 17/814,623

(22) Filed: Jul. 25, 2022

(65) Prior Publication Data

US 2023/0033032 A1  Feb. 2, 2023

(30) Foreign Application Priority Data

Jul. 28, 2021 (JP) .................................. 2021-123547

(51) Int. Cl.
| | |
|---|---|
| *H05K 1/18* | (2006.01) |
| *H05K 1/02* | (2006.01) |
| *A61B 5/25* | (2021.01) |

(52) U.S. Cl.
CPC .............. *H05K 1/0281* (2013.01); *A61B 5/25* (2021.01); *H05K 1/189* (2013.01); *H05K 2201/10151* (2013.01)

(58) Field of Classification Search
CPC ................. H05K 1/0281; H05K 1/189; H05K 2201/10151; A61B 5/25

USPC .......................................................... 361/749
See application file for complete search history.

(56) References Cited

U.S. PATENT DOCUMENTS

| | | | |
|---|---|---|---|
| 11,141,091 B2* | 10/2021 | Kumar | ...................... A61B 5/25 |
| 2021/0059586 A1* | 3/2021 | Marriott | ................... A61B 5/11 |

FOREIGN PATENT DOCUMENTS

JP   2020-198396   12/2020

\* cited by examiner

*Primary Examiner* — Binh B Tran
(74) *Attorney, Agent, or Firm* — IPUSA, PLLC

(57) ABSTRACT

A circuit board includes a support member having a first major surface and a second major surface opposite the first major surface, and an elastic interconnect substrate having a first surface and a second surface opposite the first surface, at least part of the second surface being fixed to the first major surface and the second major surface of the support member, wherein the first surface of the interconnect substrate includes a circuit region where an electronic component is mounted and at least one electrode region where at least one external electrode is arranged, wherein the circuit region is disposed indirectly on the first major surface of the support member, and wherein the interconnect substrate is bent around the support member, and at least part of the electrode region is disposed indirectly on the second major surface of the support member.

7 Claims, 7 Drawing Sheets

CIRCUIT BOARD

CROSS-REFERENCE TO RELATED APPLICATIONS

The present application is based upon and claims priority to the prior Japanese Patent Application No. 2021-123547 filed on Jul. 28, 2021, with the Japanese Patent Office, the entire contents of which are incorporated herein by reference.

FIELD

The disclosures herein relate to circuit boards.

BACKGROUND

Various circuit boards for measuring biological signals are known in the art. Such circuit boards may sometimes be configured to use a material having high elasticity for a base structure in order to increase its conformability when mounted on a living body. For example, a polymer nanosheet made of a synthetic polymer, a natural polymer, a rubber, an elastomer, or the like has been proposed as a material to be used for the base structure (e.g., see Patent Document 1).

Use of a material having flexibility or elasticity for an interconnect substrate constituting a circuit board may create, due to the expansion or contraction of the interconnect substrate, a risk of breaking the connection between the interconnect substrate and electronic components mounted thereon or a risk of failing to acquire signals in a stable manner due to changes in the distance between external electrodes used for measurement.

Accordingly, there may be a need to provide a circuit board capable of securing reliable connection with an electronic component mounted thereon and reducing changes in the distance between external electrodes.

RELATED-ART DOCUMENT

[Patent Document] Japanese Laid-open Patent Publication No. 2020-198396

SUMMARY

According to an embodiment, a circuit board includes a support member having a first major surface and a second major surface opposite the first major surface, and an elastic interconnect substrate having a first surface and a second surface opposite the first surface, at least part of the second surface being fixed to the first major surface and the second major surface of the support member, wherein the first surface of the interconnect substrate includes a circuit region where an electronic component is mounted and at least one electrode region where at least one external electrode is arranged, wherein the circuit region is disposed indirectly on the first major surface of the support member, and wherein the interconnect substrate is bent around the support member, and at least part of the electrode region is disposed indirectly on the second major surface of the support member.

The object and advantages of the embodiment will be realized and attained by means of the elements and combinations particularly pointed out in the claims. It is to be understood that both the foregoing general description and the following detailed description are exemplary and explanatory and are not restrictive of the invention, as claimed.

DESCRIPTION OF EMBODIMENTS

Figure 1:
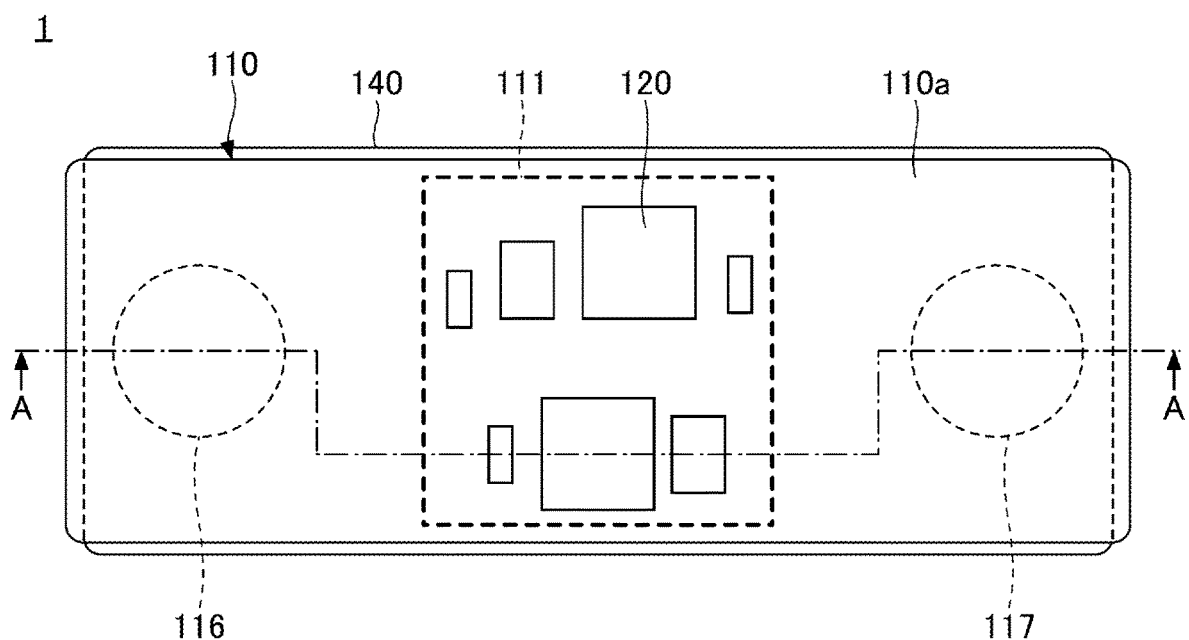
FIG. 1 is a plan view illustrating an example of a circuit board according to a first embodiment.

In the following, embodiments of the invention will be described with reference to the drawings. In each of the drawings, the same elements are referred to by the same reference numerals, and duplicate descriptions may be omitted.

First Embodiment

Figure 2:
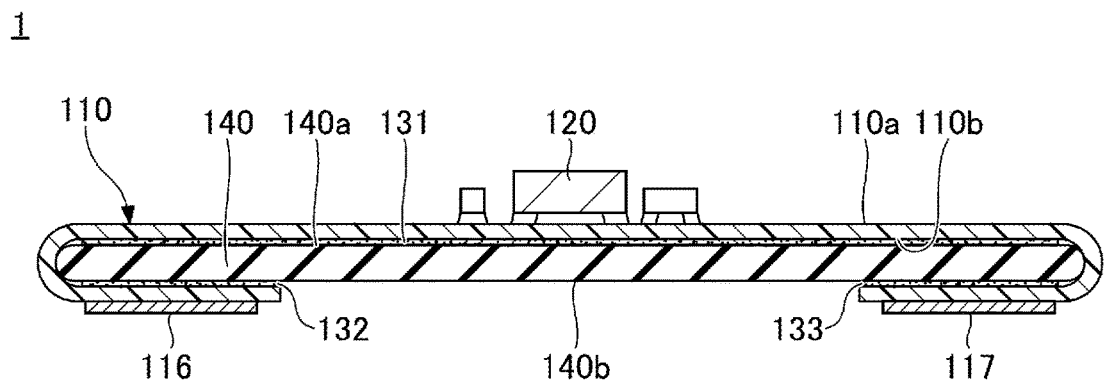
FIG. 2 is a cross-sectional view taken along the line A-A in FIG. 1.
Figure 3:
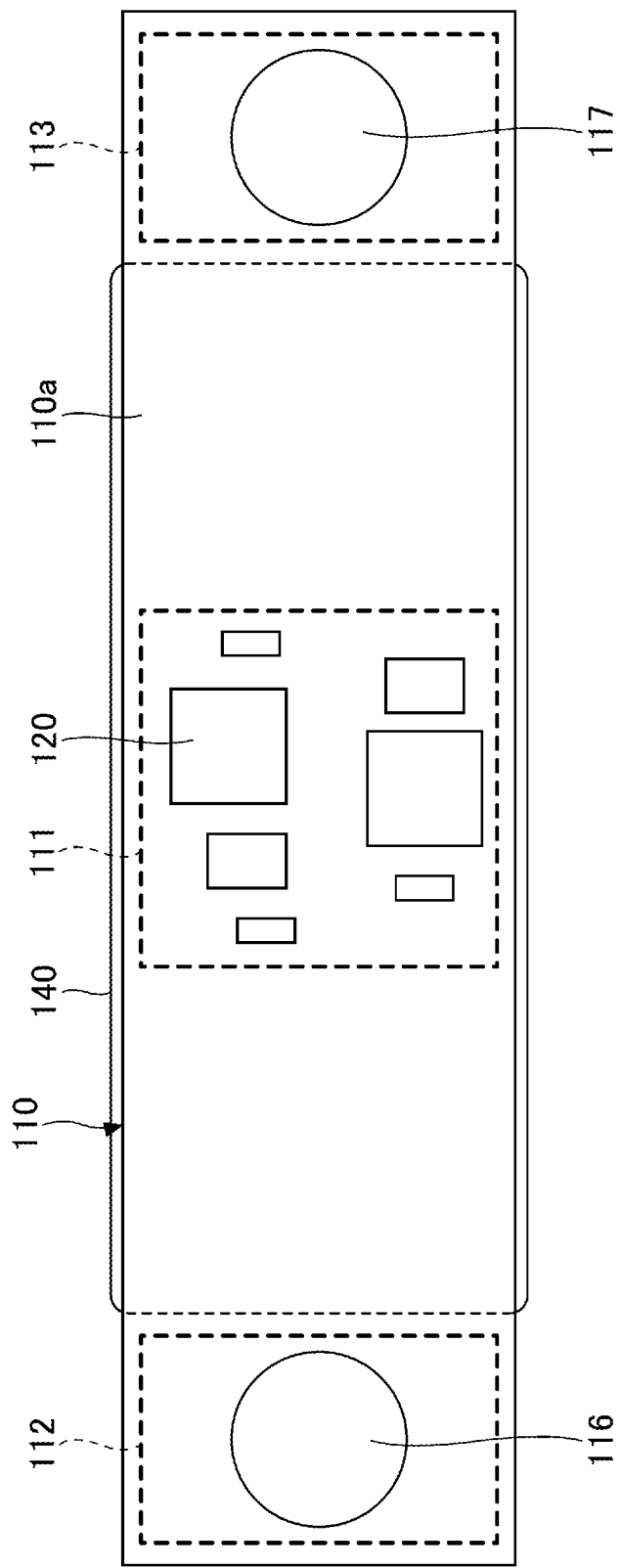
FIG. 3 is a plan view illustrating an example of an interconnect substrate of the first embodiment that is not bent.

FIG. 1 is a plan view illustrating an example of a circuit board according to a first embodiment. FIG. 2 is a cross-sectional view taken along line A-A in FIG. 1. FIG. 3 is a plan view illustrating an example of the interconnect substrate of the first embodiment that is not bent. As illustrated in FIGS. 1 to 3, a circuit board 1 includes an interconnect substrate 110, electronic components 120, adhesive layers 131 through 133, and a support member 140.

The interconnect substrate 110 is a flexible board. The interconnect substrate 110 includes, for example, an interconnect pattern, pads for mounting components, an insulating layer, etc., on an insulating resin having a low Young's modulus and flexibility. Examples of the insulating resin having low Young's modulus and flexibility include a polyimide resin, an epoxy resin, a liquid crystal polymer, and the like. The interconnect substrate 110 may be an elastic substrate made of urethane or the like. The plane shape of the interconnect substrate 110 is, for example, rectangular, but is not limited thereto. The thickness of the interconnect substrate 110 may be, for example, about 20 to 100 μm.

Referring to FIG. 3, a first surface 110a of the interconnect substrate 110 includes a circuit region 111 and electrode regions 112 and 113. In the state before the interconnect substrate 110 is bent, the circuit region 111 is provided substantially at the center of the first surface 110a in the longitudinal direction thereof. The electrode regions 112 and 113 are provided on both sides of the circuit region 111 on the first surface 110a.

The electronic components 120 are mounted on the circuit region 111. The electronic components 120 may include a semiconductor component and a passive component. The electronic components 120, for example, constitutes a circuit for processing a biological signal. Examples of the semiconductor component constituting the electronic components 120 include an integrated circuit or the like for signal processing. Examples of the passive component constituting the electronic components 120 include a resistor, a capacitor, an inductor, an antenna, a connector, and the like. No electronic components or the like are mounted on a second surface 110b of the interconnect substrate 110 opposite the first surface 110a.

An external electrode 116 is arranged in the electrode region 112, and an external electrode 117 is arranged in the electrode region 113. The plane shape of the external electrodes 116 and 117 is, for example, circular, but may alternatively be rectangular or the like. The external electrodes 116 and 117 are electrically connected to the electronic components 120 at proper locations via interconnects (not shown). The material of the external electrodes 116 and 117 may be, for example, copper or the like. The thickness of the external electrodes 116 and 117 may be, for example, about 5 to 35 μm.

Referring to FIG. 2, the second surface 110b of the interconnect substrate 110 is fixed to the support member 140 via the adhesive layers 131 through 133. The support member 140 includes a first major surface 140a and a second major surface 140b opposite the first major surface 140a, and is preferably larger than the circuit region 111 in a plan view.

The material and thickness of the support member 140 may properly be selected according to application. For example, in the case in which bending with a relatively small radius of curvature is desired, a material or thickness that is easy to bend may be selected. Examples of the material of the support member 140 include a polyethylene terephthalate film, a polyimide film, a glass epoxy substrate, and the like. The support member 140 may be flexible. The adhesive layers 131 through 133 may be, for example, an acrylic resin, an epoxy resin, or the like. The adhesive layers 131 through 133 may be provided in a liquid state, a film state, or the like, for example. The thickness of each of the adhesive layers 131 through 133 may be, for example, about 20 to 100 μm.

Specifically, a region exactly overlapping the circuit region 111 in the plan view on the second surface 110b of the interconnect substrate 110 is fixed to the first major surface 140a of the support member 140 via the adhesive layer 131. That is, the circuit region 111 of the interconnect substrate 110 is disposed indirectly on the first major surface 140a of the support member 140.

The opposite end portions of the interconnect substrate 110 are bent along both ends of the support member 140 at a flexure point between the circuit region 111 and the electrode region 112 and at a flexure point between the circuit region 111 and the electrode region 113. A region exactly overlapping the electrode region 112 in the plan view on the second surface 110b of the interconnect substrate 110 is fixed to the second major surface 140b of the support member 140 via the adhesive layer 132.

A region exactly overlapping the electrode region 113 in the plan view on the second surface 110b of the interconnect substrate 110 is fixed to the second major surface 140b of the support member 140 via the adhesive layer 133. That is, the electrode regions 112 and 113 of the interconnect substrate 110 are disposed indirectly on the second major surface 140b of the support member 140. In this manner, the circuit region 111 and the electrode regions 112 and 113 are disposed on opposite sides of the support member 140 in a cross-sectional view. Namely, the electronic components 120 and the external electrodes 116 and 117 are disposed on the opposite sides of the support member 140 in the cross-sectional view.

The circuit board 1 may be used as a sensor for detecting various kinds of biological information from a living body by placing the external electrodes 116 and 117 in contact with the living body, for example. Specifically, the circuit board 1 may be used, for example, as a myoelectric sensor. Alternatively, the circuit board 1 may be used as an electrocardiographic sensor or a magnetoencephalographic sensor.

As described above, the circuit board 1 has the interconnect substrate 110 supported by the support member 140, so that the expansion and contraction of the interconnect substrate 110 is reduced. This arrangement reduces the risk of breakage at the connection (solder, etc.) of the electronic components 120 caused by the expansion and contraction of the interconnect substrate 110, thereby ensuring reliable connection with the electronic components 120. Further, the reduction in the expansion and contraction of the interconnect substrate 110 enables the reduction of changes in the distance between the external electrode 116 and the external electrode 117. When the circuit board 1 is used as a myoelectric sensor, for example, changes in the distance between the external electrodes 116 and 117 would cause measurements to be unstable. However, the circuit board 1 is configured such that the provision of the support member 140 reduces changes in the distance between the external electrode 116 and the external electrode 117, thereby enabling the acquisition of stable measurements.

In addition, the circuit board 1 may be flexibly bent while reducing the expansion and contraction of the interconnect substrate 110 by properly selecting the material and the thickness of the support member 140. The scope of application of the circuit board 1 can thus be expanded.

In the circuit board 1, the electronic components 120 are mounted only on the first surface 110a of the interconnect substrate 110, and, also, the external electrodes 116 and 117 are disposed only on the first surface 110a of the interconnect substrate 110. With this arrangement of the circuit board 1, the electronic components 120 and the external electrodes 116 and 117 can be easily arranged on the respective, opposite surfaces of the support member 140 only by bending the interconnect substrate 110. There is no need to form an interlayer connection structure in the support member 140, which serves to reduce the cost. Since the electronic components 120 and the external electrodes 116 and 117 are arranged on the respective, opposite sides of the support member 140, the degree of freedom in layout can be improved.

First Variation of First Embodiment

A first variation of the first embodiment is directed to an example of a circuit board in which the positions of adhesive layers are different. In the first variation of the first embodiment, a description of the same components as those of the above-described embodiment may be omitted.

Figure 4:
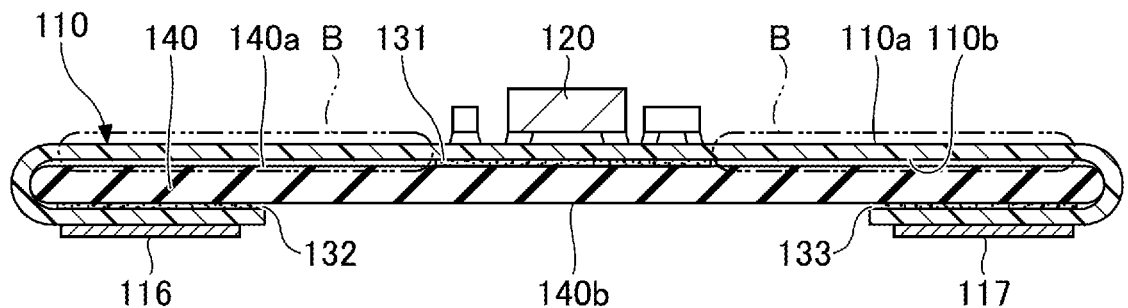
FIG. 4 is a cross-sectional view illustrating an example of a circuit board according to a first variation of the first embodiment.

FIG. 4 is a cross-sectional view illustrating an example of a circuit board according to the first variation of the first embodiment, and illustrates a cross-sectional view corresponding to that of FIG. 2. In a circuit board 1A illustrated in FIG. 4, the adhesive layer 131 may bond a portion of the second surface 110b of the interconnect substrate 110 to a portion of the first major surface 140a of the support member 140.

In the example illustrated in FIG. 4, at least a portion of the region exactly overlapping the circuit region 111 in the plan view on the second surface 110b of the interconnect substrate 110 is fixed to the first major surface 140a of the support member 140 via the adhesive layer 131. The second surface 110b of the interconnect substrate 110 includes unbonded regions B in which no adhesive layers are provided and which are situated opposite each other across the adhesive layer 131 in the plan view. Namely, the second surface 110b of the interconnect substrate 110 and the first major surface 140a of the support member 140 are not bonded to each other in the unbonded regions B that are situated opposite each other across the adhesive layer 131 in the plan view. In the unbonded regions B, the second surface 110b of the interconnect substrate 110 may be in contact with the first major surface 140a of the support member 140, or a gap may exist therebetween.

On the second surface 110b of the interconnect substrate 110, at least part of the regions facing the second major surface 140b of the support member 140 is fixed to the second major surface 140b of the support member 140 through the adhesive layers 132 and 133. On the second surface 110b of the interconnect substrate 110, the area between the adhesive layer 131 and the adhesive layer 132 in the plan view and the area between the adhesive layer 131 and the adhesive layer 133 in the plan view are the unbonded regions B.

At least part of the region exactly overlapping the electrode region 112 in the plan view on the second surface 110b of the interconnect substrate 110 is fixed to the second major surface 140b of the support member 140 via the adhesive layer 132, for example. At least part of the region exactly overlapping the electrode region 113 in the plan view on the second surface 110b of the interconnect substrate 110 is fixed to the second major surface 140b of the support member 140 via the adhesive layer 133.

Alternatively, at least part of the region exactly overlapping the external electrode 116 in the plan view on the second surface 110b of the interconnect substrate 110 may be fixed to the second major surface 140b of the support member 140 through the adhesive layer 132. At least part of the region exactly overlapping with the external electrode 117 in the plan view on the second surface 110b of the interconnect substrate 110 may be fixed to the second major surface 140b of the support member 140 through the adhesive layer 133. By providing the adhesive layers 131 through 133 at the positions illustrated in FIG. 4, the unbonded regions B are formed, and the interconnect substrate 110 can be bent relatively freely in the unbonded region B. As a result, when the interconnect substrate 110 is elastic, its function can be fully utilized. Further, when a deformable member is used for the support member 140, the interconnect substrate 110 can be stretched and contracted to conform to the deformation of the support member 140.

Second Variation of the First Embodiment

A second variation of the first embodiment is directed to an example of a circuit board having an interconnect substrate different from that of the first embodiment. In the second variation of the first embodiment, a description of the same components as those of the above-described embodiment may be omitted.

Figure 5:
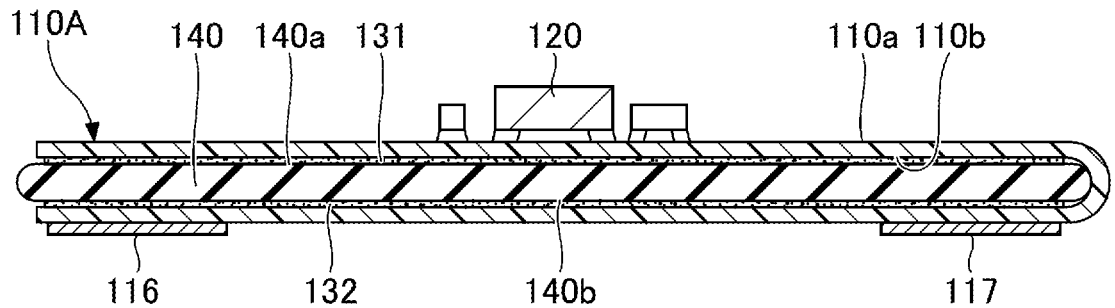
FIG. 5 is a cross-sectional view illustrating an example of a circuit board according to a second variation of the first embodiment.
Figure 6:
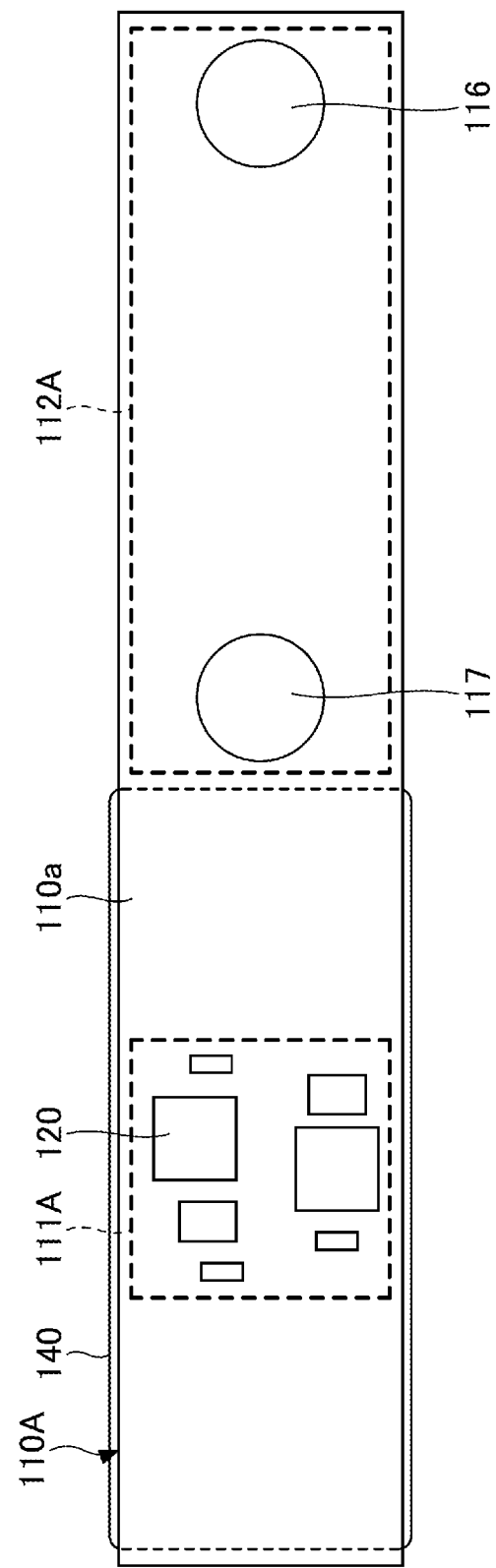
FIG. 6 is a plan view illustrating an example of an interconnect substrate of the second variation of the first embodiment that is not bent.

FIG. 5 is a cross-sectional view illustrating an example of a circuit board according to a second variation of the first embodiment, and illustrates a cross-sectional view corresponding to that of FIG. 2. FIG. 6 is a plan view illustrating the interconnect substrate of the second variation of the first embodiment that is not bent. Referring to FIGS. 5 and 6, a circuit board 1B differs from the circuit board 1 (see FIGS. 1 to 3) in that the interconnect substrate 110 is replaced with an interconnect substrate 110A.

Referring to FIG. 6, the first surface 110a of the interconnect substrate 110A includes a circuit region 111A and an electrode region 112A. In the state before the interconnect substrate 110A is bent, the circuit region 111A is situated on the first surface 110a toward one end in the longitudinal direction thereof. A plurality of electronic components 120 are mounted in the circuit region 111A. No electronic component or the like is mounted on the second surface 110b of the interconnect substrate 110A. The electrode region 112A is situated on the first surface 110a toward the opposite end in the longitudinal direction thereof, and is situated adjacent to the circuit region 111A. External electrodes 116 and 117 are arranged in the electrode region 112A.

Referring to FIG. 5, the interconnect substrate 110A on which the electronic components 120 are mounted is fixed to the support member 140 through adhesive layers 131 and 132. Specifically, a region exactly overlapping the circuit region 111A in the plan view on the second surface 110b of the interconnect substrate 110A is fixed to the first major surface 140a of the support member 140 via the adhesive layer 131. That is, the circuit region 111A of the interconnect substrate 110A is disposed indirectly on the first major surface 140a of the support member 140.

The interconnect substrate 110A is bent along an end of the support member 140 at a flexure point between the circuit region 111A and the electrode region 112A. A region exactly overlapping the electrode region 112A in the plan view on the second surface 110b of the interconnect substrate 110A is fixed to the second major surface 140b of the support member 140 via the adhesive layer 132. That is, the electrode region 112A of the interconnect substrate 110A is disposed indirectly on the second major surface 140b of the support member 140. In this manner, the circuit region 111A and the electrode region 112A are disposed on the respective, opposite sides of the support member 140 in a cross-sectional view.

As described above, in the state before the interconnect substrate 110A is bent, one electrode region 112A in which the external electrodes 116 and 117 are arranged may be provided on one side of the circuit region 111A on the first surface 110a. With this structure, the circuit board 1B provides the same effects as the circuit board 1 of the first embodiment.

Second Embodiment

The second embodiment is directed to an example of a circuit board having four external electrodes. In the second embodiment, a description of the same components as those of the above-described embodiments may be omitted.

Figure 7:
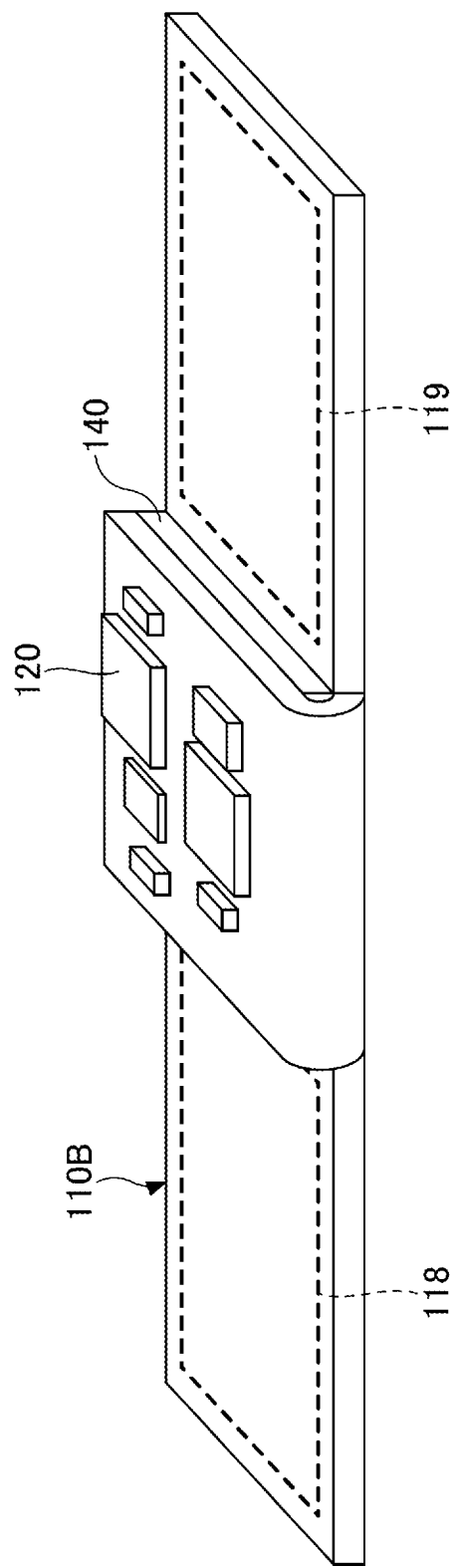
FIG. 7 is an oblique view illustrating an example of a circuit board according to a second embodiment.
Figure 8:
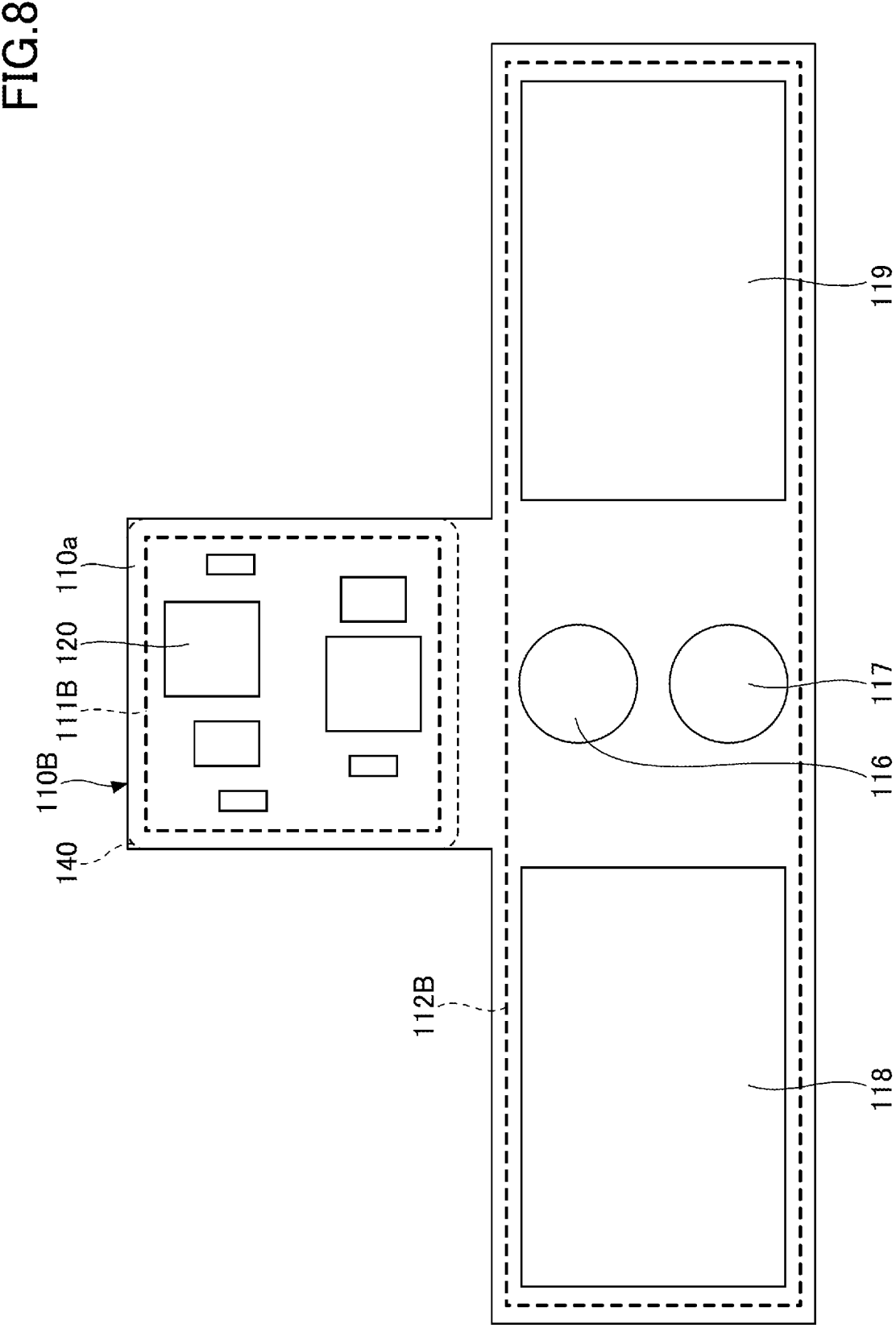
FIG. 8 is a plan view illustrating an example of an interconnect substrate of the second embodiment that is not bent.

FIG. 7 is an oblique view illustrating an example of a circuit board according to the second embodiment. FIG. 8 is a plan view illustrating an interconnect substrate of the second embodiment that is not bent. Referring to FIGS. 7 and 8, a circuit board 1C differs from the circuit board 1 (see FIGS. 1 to 3) in that the interconnect substrate 110 is replaced with an interconnect substrate 110B.

Referring to FIG. 8, a first surface 110a of the interconnect substrate 110B includes a circuit region 111B and an electrode region 112B. The electrode region 112B has a rectangular shape having four sides in a plan view, and extends in the longitudinal direction of the interconnect substrate 110B. In the state before the interconnect substrate 110B is bent, the circuit region 111B is situated on a portion of the first surface 110a that protrudes from one side (one long side) of the electrode region 112B. A plurality of electronic components 120 are mounted in the circuit region 111B. No electronic component or the like is mounted on the second surface 110b of the interconnect substrate 110B.

External electrodes 116, 117, 118, and 119 are arranged in the electrode region 112B. The external electrodes 116 and 117 are used as positive and negative electrodes, respectively, and the external electrodes 118 and 119 are used as reference electrodes. The external electrodes 116, 117, 118, and 119 are electrically connected to the electronic components 120 at proper locations via interconnects (not shown). The material and thickness of the external electrodes 118 and 119 may be substantially the same as those of the external electrodes 116 and 117, for example.

Referring to FIGS. 7 and 8, the circuit region 111B of the interconnect substrate 110B is disposed indirectly on the first major surface 140a of the support member 140. A portion of the electrode region 112B where the external electrodes 116 and 117 are arranged is disposed indirectly on the second major surface 140b of the support member 140. That is, the circuit region 111B and the portion of the electrode region 112B where the external electrodes 116 and 117 are arranged are situated on respective, opposite sides of the support member 140 in a cross-sectional view. Respective portions of the electrode region 112B where the external electrodes 118 and 119 are arranged are situated opposite each other across the support member 140 in the plan view.

With this structure, the circuit board 1C provides the same effects as the circuit board 1 of the first embodiment. For example, when the circuit board 1C is used as a myoelectric sensor, even if the interconnect substrate 110B is an elastic substrate using urethane or the like, the support member 140 prevents the distance between the external electrodes 116 and 117 used as the positive electrode and the negative electrode from changing. The circuit board 1C thus enables stable detection of myoelectric signals.

On the other hand, the respective regions where the external electrodes 118 and 119 used as reference electrodes are arranged is not restrained by the support member 140, and can freely stretch and contract. As a result, the circuit board 1C can be easily fixed to the living body by using the regions where the external electrodes 118 and 119 of the interconnect substrate 110B are arranged. The reference electrodes serve as a reference potential for myoelectric signals. The provision of the circuit board 1C with the external electrodes 118 and 119 used as reference electrodes enables more stable detection of myoelectric signals.

Figure 9:
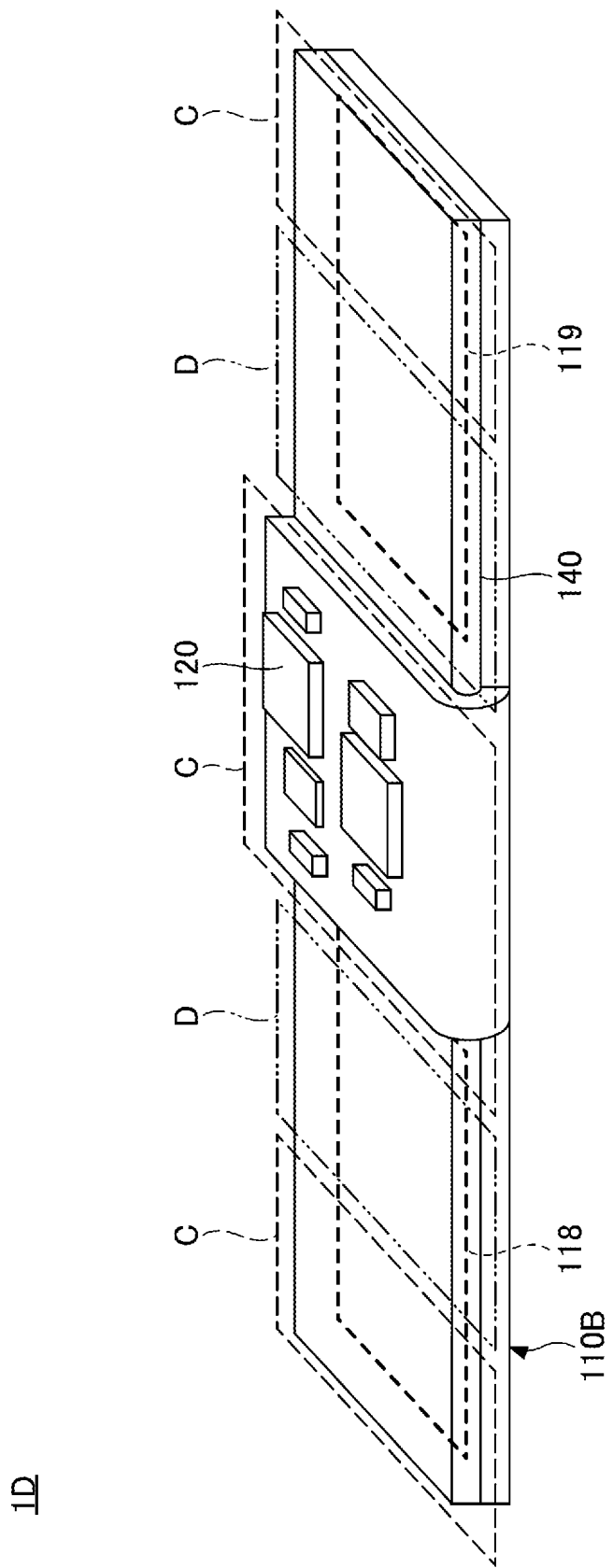
FIG. 9 is an oblique view illustrating an example of a circuit board according to a first variation of the second embodiment.

It may be noted that, as in the case of a circuit board 1D illustrated in FIG. 9, the support member 140 may be lengthened in the longitudinal direction of the interconnect substrate 110B. In this case, adhesive layers are provided between the interconnect substrate 110B and the support member 140 at the portions indicated by the dashed lines C for bonding both, for example. The portions indicated by the dash double dot lines D are unbonded regions where no adhesive layers are provided.

With the provision of the unbonded region D at the positions illustrated in FIG. 9, the use of a deformable member for the support member 140 allows the interconnect substrate 110 to conform to the deformation of the support member 140 by stretching and contracting. In FIG. 9, modification may be made such that the electrode regions for the external electrodes 118 and 119 and the portions indicated by the dashed lines C having the adhesive layers formed therein may be made substantially the same in size so that they exactly overlap each other.

According to at least one embodiment, a circuit board is provided that is capable of securing reliable connection with an electronic component mounted thereon and reducing changes in the distance between external electrodes.

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification relate to a showing of the superiority and inferiority of the invention. Although the embodiment(s) of the present inventions have been described in detail, it should be understood that the various changes, substitutions, and alterations could be made hereto without departing from the spirit and scope of the invention.

What is claimed is:

1. A circuit board comprising:
a support member having a first major surface and a second major surface opposite the first major surface; and
an elastic interconnect substrate having a first surface and a second surface opposite the first surface, at least part of the second surface being fixed to the first major surface and the second major surface of the support member,
wherein the first surface of the interconnect substrate includes a circuit region where an electronic component is mounted and at least one electrode region where at least one external electrode is arranged,
wherein the circuit region of the first surface is disposed indirectly on the first major surface of the support member, such that a region on the second surface directly opposite the circuit region faces the first major surface of the support member, and
wherein the interconnect substrate is bent around the support member, and at least part of the electrode region of the first surface is disposed indirectly on the second major surface of the support member, such that a region on the second surface directly opposite the at least part of the electrode region faces the second major surface of the support member.

2. The circuit board as claimed in claim 1, wherein the at least one electrode region is a single electrode region where a plurality of external electrodes are arranged, and is provided on the first surface on one side of the circuit region in a state before the interconnect substrate is bent, and
wherein the interconnect substrate is bent around the support member and at a flexure point between the circuit region and the electrode region, and at least part of the electrode region is disposed indirectly on the second major surface of the support member.

3. The circuit board as claimed in claim 1, wherein the at least one electrode region is a plurality of electrode regions, and the electrode regions are provided on the first surface on both sides of the circuit region in a state before the interconnect substrate is bent, wherein the interconnect substrate is bent around the support member and at flexure points between the circuit region and the electrode regions, and the electrode regions are disposed indirectly on the second major surface of the support member.

4. The circuit board as claimed in claim 2, wherein the electrode region has four sides in a plan view, and, in a state before the interconnect substrate is bent, the circuit region is situated on a portion of the first surface that protrudes from one side of the electrode region.

5. The circuit board as claimed in claim 2, wherein the at least one external electrode arranged in the electrode region includes four external electrodes, and wherein a region where two of the four external electrodes are arranged is disposed indirectly on the second major surface of the support member, and respective regions where the other two of the four external electrodes are arranged are disposed opposite each other across the support member in a plan view.

6. The circuit board as claimed in claim 1, wherein at least part of a region exactly overlapping the circuit region in a plan view on the second surface is fixed to the first major surface of the support member via a first adhesive layer, and wherein the second surface has unbonded regions where no adhesive layer is provided, the unbonded regions being situated opposite each other across the first adhesive layer in the plan view.

7. The circuit board as claimed in claim 6, wherein at least part of a region, on the second surface, facing the second major surface of the support member is fixed to the second major surface of the support member via a second adhesive layer, and wherein on the second surface, a region between the first adhesive layer and the second adhesive layer in the plan view is one of the unbonded regions.

* * * * *